United States Patent [19]

Jacob

[11] Patent Number: 5,087,418
[45] Date of Patent: * Feb. 11, 1992

[54] PROCESS FOR DRY STERILIZATION OF MEDICAL DEVICES AND MATERIALS

[76] Inventor: Adir Jacob, 23 Juniper La., Framingham, Mass. 01701

[*] Notice: The portion of the term of this patent subsequent to Jan. 31, 2006 has been disclaimed.

[21] Appl. No.: 576,356

[22] Filed: Aug. 31, 1990

Related U.S. Application Data

[63] Continuation-in-part of Ser. No. 275,325, Nov. 22, 1988, which is a continuation of Ser. No. 19,134, Feb. 25, 1987, Pat. No. 4,801,427, and a continuation-in-part of Ser. No. 562,392, Aug. 3, 1990, which is a continuation of Ser. No. 331,438, Mar. 31, 1989, Pat. No. 4,976,920, which is a continuation-in-part of Ser. No. 72,899, Jul. 14, 1987, Pat. No. 4,818,488, which is a continuation-in-part of Ser. No. 19,134, Feb. 25, 1987, Pat. No. 4,801,427.

[51] Int. Cl.$^5$ .................................................. A61L 2/14
[52] U.S. Cl. ........................................... 422/23; 422/22; 422/906; 422/907; 422/28; 204/164; 250/424; 250/472.1
[58] Field of Search .................................. 422/21–23, 422/28, 33, 906, 36, 907, 37; 250/424, 492.1; 204/164

[56] References Cited

U.S. PATENT DOCUMENTS

| | | | |
|---|---|---|---|
| Re. 30,505 | 2/1981 | Jacob | 156/643 |
| 3,383,163 | 5/1968 | Menashi | 21/54 |
| 3,701,628 | 10/1972 | Ashman et al. | 21/54 R |
| 3,753,651 | 8/1973 | Boucher | 21/54 R |
| 3,757,733 | 9/1973 | Reinberg | 118/49.5 |
| 3,876,373 | 4/1975 | Glyptis | 422/23 |
| 3,879,597 | 4/1975 | Bersin et al. | 219/121 |
| 3,923,568 | 12/1975 | Bersin | 156/8 |
| 3,951,709 | 4/1976 | Jacob | 156/8 |
| 3,971,684 | 7/1976 | Muto | 156/13 |
| 3,994,793 | 11/1976 | Harvilchuck et al. | 204/192 |
| 4,026,742 | 5/1977 | Fujino | 156/643 |
| 4,028,155 | 6/1977 | Jacob | 156/643 |
| 4,030,967 | 6/1977 | Ingrey et al. | 156/643 |
| 4,073,669 | 2/1978 | Heinecke et al. | 156/643 |
| 4,163,891 | 8/1979 | Komatsu | 219/121 |
| 4,182,646 | 1/1980 | Zajac | 156/643 |
| 4,207,286 | 6/1980 | Gut Boucher | 422/21 |
| 4,208,241 | 6/1980 | Harshbarger et al. | 156/643 |
| 4,211,601 | 7/1980 | Mogab | 156/643 |
| 4,214,946 | 7/1980 | Forget et al. | 156/643 |
| 4,226,665 | 10/1980 | Mogab | 156/643 |
| 4,229,247 | 10/1980 | Chiu et al. | 156/643 |
| 4,255,230 | 3/1981 | Zajac | 156/643 |
| 4,256,534 | 3/1981 | Levinstein et al. | 156/643 |
| 4,264,409 | 4/1981 | Forget et al. | 156/643 |
| 4,267,013 | 5/1981 | Iida et al. | 156/643 |
| 4,298,443 | 11/1981 | Maydan | 204/192 E |
| 4,314,874 | 2/1982 | Abe et al. | 156/628 |
| 4,314,875 | 2/1982 | Flamm | 156/643 |
| 4,341,592 | 7/1982 | Shortes et al. | 156/643 |
| 4,341,616 | 7/1982 | Nagatomo et al. | 204/298 |
| 4,353,777 | 10/1982 | Jacob | 156/643 |
| 4,358,686 | 11/1982 | Kinoshita | 204/298 |
| 4,362,632 | 12/1982 | Jacob | 422/183.04 |
| 4,505,782 | 3/1985 | Jacob et al. | 156/643 |
| 4,569,895 | 2/1986 | Willett et al. | 430/70 |
| 4,643,876 | 2/1987 | Jacobs et al. | 422/23 |
| 4,756,882 | 7/1988 | Jacobs et al. | 422/23 |
| 4,801,427 | 1/1989 | Jacob | 422/23 |

FOREIGN PATENT DOCUMENTS

| | | |
|---|---|---|
| 0207417 | 7/1976 | European Pat. Off. |
| 56148354 | 4/1980 | Japan |
| 58103460 | 12/1981 | Japan |
| 6389162 | 10/1986 | Japan |
| 192703 | 1/1988 | Japan |

OTHER PUBLICATIONS

*Glow Discharge Polymerization*, Modes of Electric Discharge, H. Yasuda, Journal of Polymer Science: Macromolecular Reviews, vol. 16, pp. 207–212 (Wiley, 1981).
*Plasma Treatment*, Peter W. Rose et al, Plastics Finishing and Decoration edited by Donates Satas, pp. 90–100.

Primary Examiner—Robert J. Warden
Assistant Examiner—Lyle A. Alexander
Attorney, Agent, or Firm—Lahive & Cockfield

[57] ABSTRACT

A process for dry sterilization of medical or dental devices and materials in which these materials are subjected to an electrical discharge in a hydrogen peroxide to produce an active low temperature plasma for surface sterilization and treatment of the devices and materials.

7 Claims, 3 Drawing Sheets

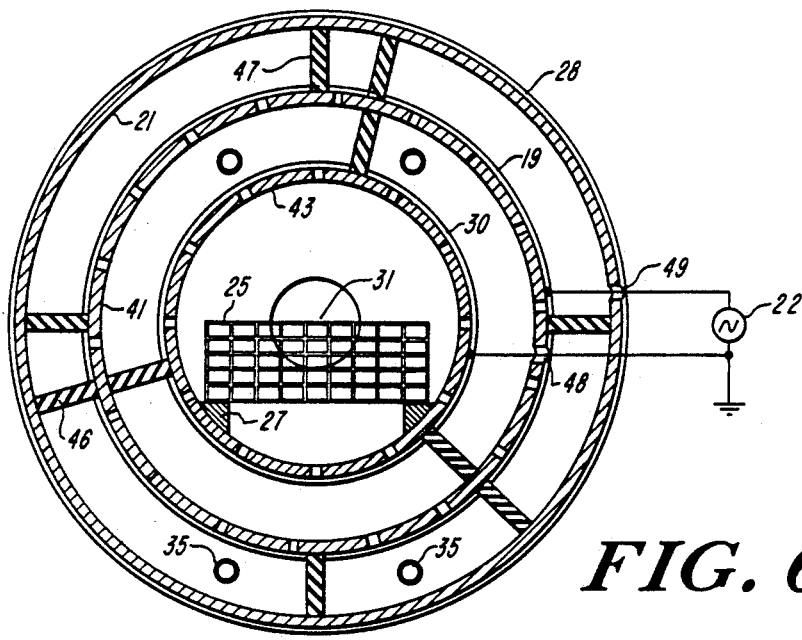
FIG. 6
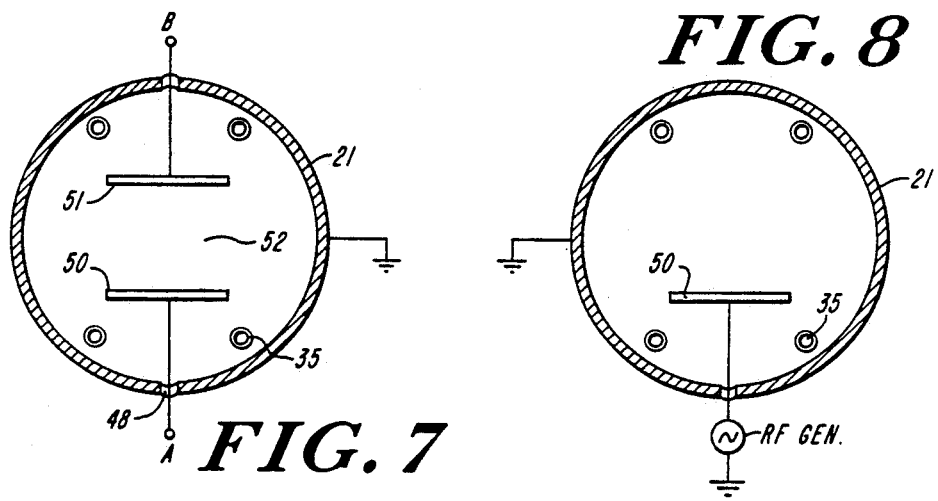
FIG. 7  FIG. 8
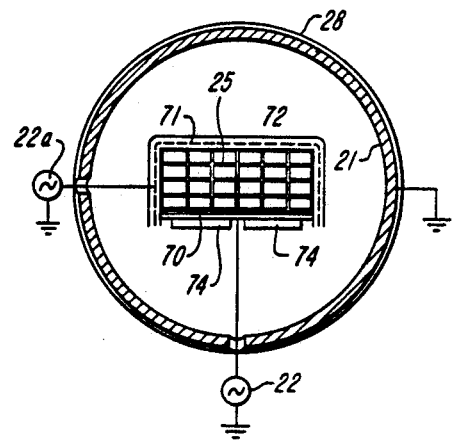
FIG. 9

PROCESS FOR DRY STERILIZATION OF MEDICAL DEVICES AND MATERIALS

BACKGROUND OF THE INVENTION

This is a Continuation-In-Part of U.S. Patent Application Ser. No. 275,325, filed Nov. 22, 1988 pending, which is a Continuation of U.S. Patent Application Ser. No. 019,134 filed Feb. 25, 1987, issued as U.S. Pat. No. 4,801,427 on Jan. 31, 1989. It is also a Continuation-In-Part of United States Patent Application Ser. No. 562,392 filed Aug. 3, 1990 pending which is a Continuation of United States Patent, Application Ser. No. 331,438 filed Mar. 31, 1989, now U.S. Pat. No. 4,976,920 which is a Continuation-In-Part of United States Patent Application Ser. No. 072,899 filed July 14, 1987, issued as U.S. Pat. No. 4,818,488 on Apr. 4, 1989 which is a Continuation-In-Part of United States Patent Application Ser. No. 019,134 filed Feb. 25, 1987, issued as U.S. Pat. No. 4,801,427 on Jan. 31, 1989.

Modern medical and dental practice require the use of aseptic materials and devices, many of them meant for repeat use. In order to achieve this asepsis, sterilization processes are needed, at the manufacturer, and also at the hospitals or dental offices for treatment of reusable materials and devices.

Typical of materials which are reused in the hospital environment and require repeated sterilization are major surgical instruments minor surgical kits, respiratory sets, fiber optic instrumentation (endoscopes, proctoscopes, angioscopes, bronchioscopes), breast pumps, etc. Typical instruments and devices which are reused in a dental environment and require repeated sterilization are hand-pieces, dental mirrors, plastic tips, model impressions and fabrics.

There are a wide variety of medical devices and materials that are to be supplied from the manufacturer already packaged and sterile. Many of these devices and materials are disposable. Typical of this group are barrier packs, head coverups and gowns, gloves, sutures, syringes and catheters.

One major sterilization process in present use is that which employs ethylene oxide (EtO) gas in combination with Freon-12 ($CCl_2F_2$) at up to three atmospheres of pressure in special shatter-proof sterilization chambers. This process, in order to achieve effective asepsis levels, requires exposure of the materials to the gas for at least one to three hours followed by a minimum of twelve hours, or longer, aeration period. The initial gas exposure time is relatively long because the sterilization is effected by alkylation of amino groups in the proteinaceous structure of any microorganism. EtO sterilization requires the attachment of the entire EtO molecule, a polyatomic structure containing seven atoms to the protein. This is accompanied by the requirement of hydrogen atom rearrangement on the protein to enable the attachment of EtO. Because of kinetic space-hindrance factors governing the attachment of such a bulky molecule, the process needs to be carried out at high pressure and be extended over a long period of time. It is, therefore, deemed very inefficient by the industry at large.

Perhaps the chief drawback to this system, however, is its dangerous toxicity. Ethylene-oxide (EtO) is a highly toxic material dangerous to humans. It was recently declared a carcinogen as well as a mutagen. It requires a very thorough aeration process following the exposure of the medical materials to the gas in order to flush away toxic EtO residues and other toxic liquid by-products like ethylene glycol and ethylene chlorohydrin. Unfortunately, it is a characteristic of the gas and the process that EtO and its toxic by-products tend to remain on the surface of the materials being treated. Accordingly, longer and longer flush (aeration) times are required in order to lower the levels of these residues absorbed on the surface of the materials to a safe operational value. A typical volume for each batch using this EtO process is 0.2 to 50 cu. ft. within the health and dental care environments.

A number of other approaches for performing sterilization have also been employed. One such process is high pressure steam autoclaving. However, this requires high temperature and is not suitable for materials which are affected by either moisture or high temperature, e.g., corrodable and sharp-edged metals, plastic-made devices, etc., employed by the hospital and the dental communities.

Another approach utilizes either x-rays or radioactive sources. The x-ray approach is difficult and expensive. The use of radioactive sources requires expensive waste disposal procedures, as well as requiring radiation safety precautions. The radiation approach also Presents problems because of radiation-induced molecular changes of some materials, which, for example, may render flexible materials brittle, e.g., catheters.

Other approaches have employed gas plasmas with various gases in processes for sterilization of materials. Of particular interest are U.S. Pat. Nos. 4,643,876 and 4,756,882 which are directed to processes employing hydrogen peroxide liquid solution or hydrogen peroxide vapor followed by generation of a plasma around the material to be sterilized.

It is therefore a primary object of the present invention to provide a process and apparatus for dry sterilization of medical and dental devices and materials, which can be operated efficiently, both with respect to time and volume and which can be carried out below 70° C.

It is another object of the present invention to provide a safe, nontoxic, process for the sterilization and surface treatment of medical and dental devices and materials, a process which does not employ toxic feed gases and one which does not yield toxic absorbed surface residues and by-products.

SUMMARY OF THE INVENTION

Broadly speaking in the present invention, sterilization or surface treatment is achieved by exposing the medical or dental devices and materials to hydrogen peroxide vapor under dynamic flow-through conditions and then initiating a gas discharge plasma in the vapor. The plasma discharge chemical-physical parameters can be adjusted to fit almost any practical application of sterilization and surface treatment. While residual hydrogen peroxide levels are quite low (<20 ppm) at the end of the sterilization process, it could be followed by a separate, in-situ, plasma process to effect further reduction of hydrogen peroxide residuals to levels of 1 ppm or less.

Such plasmas are generated by creating an electrical discharge in a gaseous atmosphere maintained at subatmospheric or atmospheric pressure, within which the materials to be sterilized are placed.

Generation of gas plasmas is a very well developed discipline, which has been specifically employed in semiconductor processing. See, for example, U.S. Pat.

Nos. 3,951,709; 4,028,155; 4,353,777; 4,362,632; 4,505,782 and RE 30,505 assigned to the present inventor, as well as in sterilization techniques by others, see, for example, U.S. Pat. Nos. 3,851,436 and 4,348,357 employing oxygen gas.

In one instance the gas plasma sterilization process of this invention involves evacuating a chamber to a relatively low pressure after the devices or materials to be sterilized or treated have been placed within it.

Hydrogen peroxide vapor, as an example, is then provided to the chamber at a relatively low pressure, typically in the range 0.3 to 2 mmHg, with a continuous dynamic flow rate in the range of 30–300 milligrams per minute. An electrical discharge is produced within the chamber by conventional means, such as a microwave cavity or a radio frequency (RF) excited electrode. Alternatively, RF power in the power density range 0.0125–0.08 W/cm$^3$ may be coupled into the gas via a single electrode disposed within the chamber in a non-symmetrical electrical configuration, or via two electrodes contained within the chamber in an electrically symmetrical configuration. In either case the material to be sterilized is placed on one of the electrodes, while the chamber's wall is commonly maintained at ground potential.

The nonsymmetrical arrangement provides the basis for a low plasma potential mode of operation which is conducive to low sterilization temperatures and the suppression of otherwise deleterious ion bombardment and contamination of the devices and materials.

The resultant discharge produces a gas plasma including both excited electrically charged gaseous species and excited electrically neutral gaseous species. For example, free hydroxl (OH) radicals are formed in a discharge through hydrogen peroxide, which are characterized by substantial bactericidal and sporocidal potency. These active species interact chemically with the proteinaceous components of the microorganisms residing on the surfaces of medical or dental devices to be sterilized. More specifically, hydroxyl (OH) radicals, formed during the plasma discharge through hydrogen peroxide vapor, will either chemically abstract hydrogen atoms from the back bone or the side chains of microorganisms' DNA molecular structures, or preferentially attack chemical double bonds by attaching themselves to carbon atoms on such structures, thereby denaturing the proteinaceous molecules and achieving kill rates of microorganisms equivalent to a probability of microorganism survival of less than one in a million.

Reduction of hydrogen peroxide residuals on sterilized surfaces to practically insignificant levels can be achieved by a plasma discharge through gaseous oxygen, argon, or through a binary mixture of argon/oxygen, in which oxygen constitutes less than 5% by volume, in the dynamic flowrate range 50–500 standard cubic centimeter per minute, in the pressure range 0.3–3 mmHg, at a power density range 0.013–0.08 W/cc, coupled with an exposure duration of less than one hour.

DESCRIPTION OF THE DRAWINGS

In the drawing

FIGS. 6, 7, 8, 9, 10, 11, 12 and 13 are cross sectional and side views of alternative embodiments.

DESCRIPTION OF PREFERRED EMBODIMENTS

Figure 1:
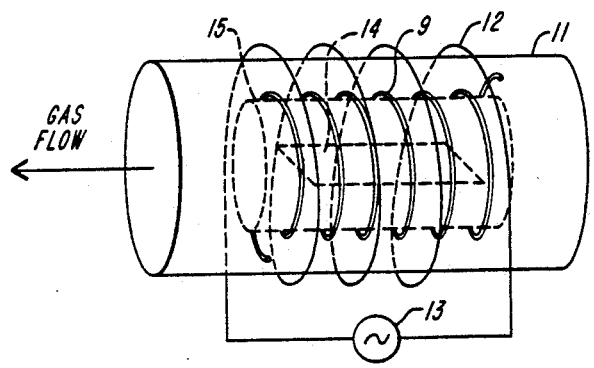
FIG. 1 is a general diagrammatic illustration of an apparatus suitable for use in the practice of this invention.

FIG. 1 is a general diagrammatic illustration of an RF excited discharge chamber of the type used in the process of this invention, although configurations other than the depicted cylindrical form would be as efficient. The cylindrical chamber 11 is formed, in this instance, of glass or quartz and encloses within it the material 14 to be treated. The chamber is commonly connected to a mechanical vacuum pump (not shown) that establishes sub-atmospheric pressure conditions within the chamber. An exciter coil 12 couples RF energy from RF source 13 to the gas enclosed within the gas tight chamber creating a plasma therein.

Alternatively, a microwave discharge cavity operating at 2,450 MHz may replace the RF exciter coil to couple power into the hydrogen peroxide vapor. An electrical discharge may be initiated and maintained within the chamber. In the gas plasma formed by such a discharge a number of excited species, both molecular and atomic, are formed. The interaction of these species with a surface of the device or material to be sterilized accomplishes the sterilization in the manner described above. The time duration of the process needed to achieve satisfactory sterilization will vary with other parameters of the discharge such as gas flow, pressure, RF or microwave power density, and load size.

Figure 2:
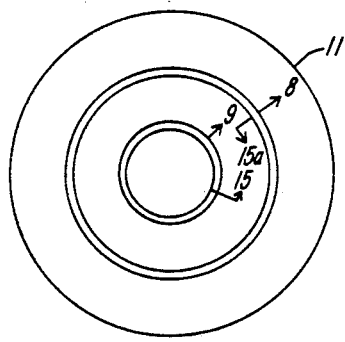
FIG. 2 is a cross sectional view of another apparatus suitable for use in the practice of this invention.

In the embodiment illustrated in FIG. 1 the apparatus includes an inner perforated metallic cylinder 15 mounted generally concentric with the long axis of the chamber 11, to form within the perforated cylinder a substantially glowless, field-free zone. The perforated cylinder 15 is electrically-floating and may, but need not be cooled by recirculating a suitable coolant (e.g., a 50–50 mixture of water and ethylene glycol) through cooling coils 9 wrapped around the cylinder's length, to effect low sterilization temperatures (<70° C.). Still lower sterilization temperatures could be effected with two concentric perforated metallic cylinders 15 and 15a, which also may be surrounded by cooling coils 9 and 8, respectively, and enclosed by non-conducting chamber 11, as shown in FIG. 2. Energy coupling into this chamber is accomplished in a similar manner as described in FIG. 1.

The resultant glowless and field-free zone within the confines of the electrically-floating perforated cylinders could be ascribed to electrical faraday-cage effects, coupled with catalytic deactivation of active species, which are the precursors of visible emission, on the metallic surface of the perforated cylinder.

Figure 3:
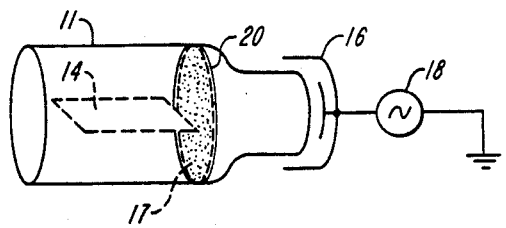
FIG. 3 is a generally diagrammatic illustration of another apparatus suitable for use in the practice of this invention.

When, as illustrated in FIG. 3, a microwave energy source 18 at for example, 2,540 MHz. is employed in lieu of the RF generator 13, the perforated metallic cylinder cannot be mounted concentric about the long axis of the chamber. Instead, the microwave cavity 16 is mounted at one end of a metallic or non-metallic chamber 11, and a perforated metallic shield 17 which may be cooled by coolant-recirculating coils 20 may be placed just beyond it toward the opposite end of the chamber, spanning the entire diameter cross section of the chamber, thus creating a field-free and glowless reactive zone immediately below it and away from the microwave cavity. These arrangements permit material 14 placed within this zone to be generally isolated from electrically charged species, while allowing the electrically neutral reactive plasma species, such as, for example, oxygen radicals, to interact with the surface of the material to be sterilized. In this manner, sterilization is commonly effected at substantially lower process temperatures.

Alternatively, the perforated metallic shield 17 may be removed, if the microwave cavity 16 is remotely located from material 14.

Microwave discharges lend themselves to this mode of operation, since the effectiveness of neutral active species generated in such a discharge survive substantial distances downstream, and away from, the microwave cavity itself. This is a direct consequence of the higher population of electrons in microwave plasmas, and consequently the higher degree of ionization and dissociation in these discharges. Also, microwave plasma electric probe measurements indicated plasma potentials nearly equal to ground potential, thereby practically eliminating energic particle bombardment during processing. This mode of operation is thus well suited for low temperature exposure of heat—sensitive devices and material, even for extended periods of sterilization time.

In the most preferred embodiments, the chamber is formed of a metallic electrically grounded and water-cooled outer shell with either a single internal perforated cylindrical shield electrode, as shown in FIG. 1, or perhaps with two such metallic shields, as shown in FIG. 2, which may be also purposely cooled, the RF energy being coupled, in the former configuration between the perforated electrode and the metallic chamber and in this latter configuration, between the two conducting perforated cylinders. In either case, conditions for low plasma potentials will prevail, with the discharge glow being confined to the space between the inner wall of the chamber and the surface(s) of the perforated cylinder(s), leaving the work volume defined by the inner perforated cylinder substantially field-free, and the workload contained therein free of contact with the plasma glow and, therefore, free of ion-bombardment, thereby eliminating device and material surface damage commonly associated with direct exposure of material to a luminous plasma glow.

This mode of operation deviates substantially from the one disclosed in U.S. Pat. Nos. 4,643,876 and 4,756,882, for which a hydrogen peroxide plasma is generated around the items to be sterilized without any shielding member protecting the workload from ensuing adverserial surface effects.

It is worth nothing, that the present invention utilizes the perforated shielding electrode as means to moderate or neutralize any adverse electrical mismatch effects due to routine hospital sterilization load variations from run to run.

This attribute allows for a constant electrical, factor pre-matched, plasma load to be "seen" by the power generator, irrespective of the nature or composition of the sterilization load. The power generator "sees" as it loads only the plasma glowing volume exterior to the work volume defined by the interior volume of the perforated electrode. The glowing plasma load changes insignificantly with the variable sterilization loads placed within the confines of the perforated electrode, since the latter acts as an electrically-shielding Faraday-Cage.

This assures an optimized power transfer to the hydrogen peroxide vapor for the creation of a corresponding plasma discharge, without using costly automatic (servomechanisms) for matching variable sterilization loads to the power generator. Since such automatic tuners are needed with modes of operation described by the related prior art, system's material and labor costs are burdened by a dollar amount about equal to that associated with the power generator itself—the most costly component of the sterilization system.

Figure 4:
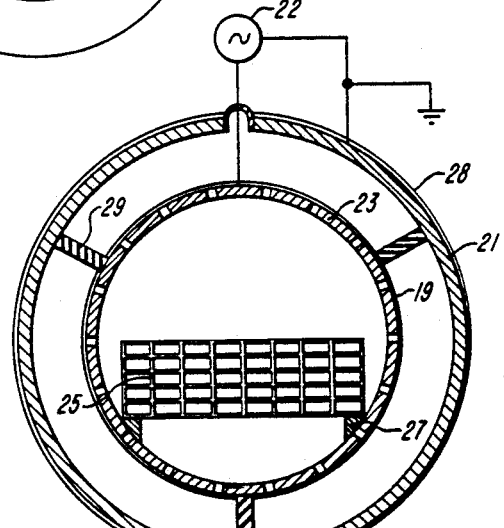
FIG. 4 is a cross sectional view of another embodiment of a sterilization chamber for use in the practice of the invention.
Figure 5:
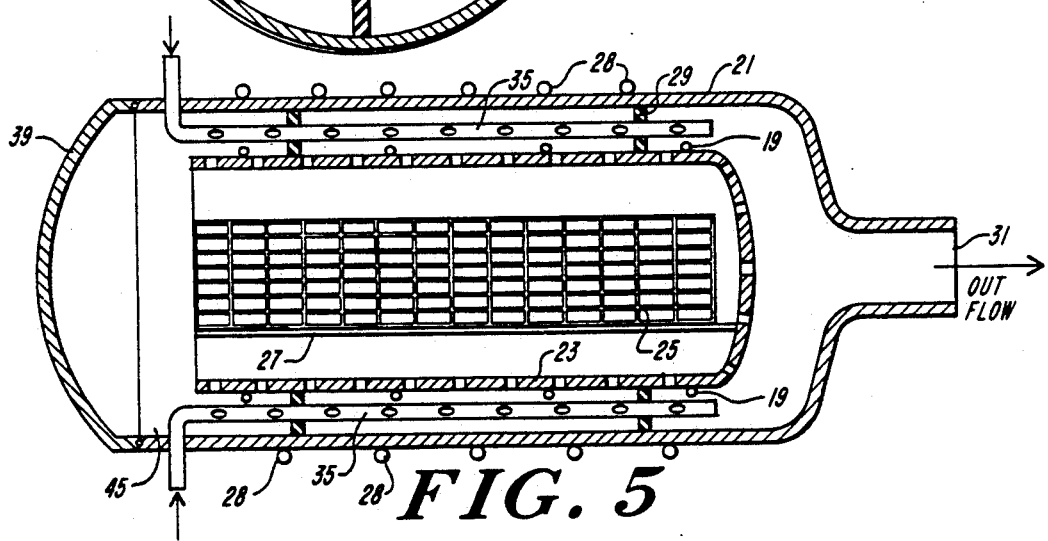
FIG. 5 is a side view of the apparatus of FIG. 4.

One such chamber configuration is illustrated in FIGS. 4 and 5. The cylindrical outer wall 21, typically formed of aluminum or stainless steel, is maintained at ground potential and serves as the chamber enclosure. This enclosure may be water-cooled with the aid of cooling coils 28 wrapped around it. Suitable dimensions for this chamber are a diameter of 36" and a length of 48". A metallic perforated inner cylinder 23 cooled by cooling coils 19 is mounted on insulating spacers 29 within the chamber so that it is positioned generally parallel with the long axis of the outer wall 21 of the chamber and concentric with it. These spacers may be formed of any suitable non-reactive and insulating type of material such as ceramic. The cylinder perforations are typically 2.5–4 mm diameter holes spaced in all directions from one another by approximately 0.5 cm in a triangulated manner. Longitudinal support rails 27 are fastened to the inner wall of the perforated cylinder 23 to support a wire basket 25 in which the materials and devices to be sterilized are placed. A suitable RF source 22 is coupled between the grounded outer chamber wall 21 and the perforated inner cylinder 23. Usually this RF source should be capable of producing an RF output in the range 0.01 to 0.1 W/cm$^3$ at frequencies in the 10–100 kilohertz or 13–27 megahertz range.

As illustrated in FIG. 5, an evacuation port 31 at the end of cylinder 21 is connected to a pump (not shown) and provides for suitable evacuation of the chamber and for continuous gas flow during the sterilization process. The vapor supplied for the discharge is generally flowed through the chamber by means of perforated diffusion tubes 35. Alternately, gas may be introduced into the chamber via a gas dispersion device (not shown) mounted behind chamber door 39 from the inside.

Material to be sterilized may be placed within wire basket 25 resting on rail 27 through the entry port behind chamber door 39. Chamber door 39 may be any suitable closure that can be conveniently opened and closed and left in a sealed position during evacuation and the gas discharge operation.

FIG. 6 illustrates a second preferred embodiment of the apparatus for practicing the process of the invention. In this configuration, the outer chamber wall 21 may be water-cooled by cooling coils 28, is again formed of metal, such as electrically grounded aluminum or stainless steel, and is of similar dimensions to that illustrated in FIG. 4. Mounted within the chamber is an inner concentric cylinder 43 formed of a perforated metal which may be purposely cooled by cooling coils 30, and is supported on insulating support struts 46. The spacing between the inner wall of the chamber and the perforated interior cylinder may range typically from 10 to 17 cm, where the chamber has an I.D. of 36".

A second metallic perforated cylinder 41 is concentrically mounted intermediate between the inner perforated cylinder 43 and the inner wall of the chamber and may also be cooled by cooling coils 19. This second perforated cylinder is supported on insulating struts 47 and is spaced typically 4 to 7 cm away from the inner perforated cylinder 43. The insulator struts may again be formed of a ceramic material. Mounted on the interior of the inner concentric cylinder 43 are support rails 27 for carrying a wire basket which would contain the materials to be sterilized. Both the outer chamber wall 21 and the inner perforated cylinder 43 are electrically connected to point of potential reference (ground). Electrical connections would most usually be made through ceramic seal feedthroughs 48 and 49. The intermediate cylinder 41 is electrically connected to one side of the RF power supply 22, the other side of which is connected to the point of potential reference.

While a variety of conventional RF sources may be used, the most typical value for the RF frequency is 13.56 MHz or, alternatively, 10–100 KHz. As in the embodiment of FIG. 5 longitudinally extending gas diffusion tubes 35 may be employed to provide the gas to the interior of the chamber. Typically each tube would have holes of diameter between 0.5 and 1.5 mm, spaced approximately 1" apart along its length. The hole diameters closer to the gas source would be of the smaller diameter. Alternatively, gas inlets may be provided behind chamber door 39. As indicated in the embodiments of FIGS. 4, 5 and 6 the perforated inner cylinders may be open-ended at both ends or, may be closed with the same perforated stock as is used to form the cylinder(s). The sterilization chambers shown in FIGS. 4, 5 and 6 may be connected to a microwave discharge source, typically operating at 2,540 MHz, in lieu of an RF energy source. In this case, the concentric perforated metallic cylinder(s) may be replaced by a single perforated shield in accordance with the operational description given for FIG. 3.

FIG. 7 illustrates a third preferred embodiment of the apparatus for practicing the process of the invention. In this diagrammatic description the outer chamber wall 21 is again formed of metal, such as aluminum or stainless steel, and is of similar dimensions to that illustrated in FIG. 4. Mounted within the chamber are two planar, metallic, electrodes 50 and 51, preferably constructed of aluminum which may be coated with insulating aluminum oxide. The gap 52 between electrodes 50 and 51, is adjustable by virtue of the movable bottom electrode 50. Terminals A and B are connected to the electrodes via an insulating feedthrough 48. The outer end of these terminals may be connected to an RF source (not shown) in such a way that when terminal B is connected to a ground potential, terminal A must be connected to the RF source, or vice versa, providing for an electrical symmetrical configuration. The work load to be sterilized is placed on lower electrode 50.

It is important to maintain the distance between the electrodes always smaller than the distance of the RF-powered electrode's edge to the grounded chamber's wall. This enables a well defined and intense plasma glow to be confined to space 52 between the electrodes and prevents deleterious sparking. The electrode material may also be made of the perforated stock previously mentioned. However, it is desirable to have the RF-powered electrode made of solid stock to enable very efficient water-cooling of that electrode. The bottom electrode may also be made of solid stock to enable a cooler surface upon which the work load to be sterilized will be placed. This chamber will commonly be evacuated to 10–100 microns Hg before gas introduction via the perforated gas diffusion tubes 35. Practical device sterilization can be obtained with process parameters for gas flow rates in the range 50–500 standard cubic centimeter per minute, in a total sterilization reaction pressure of 0.3–2 mmHg, at a range of RF power densities of 0.0125–0.08 W/cc. Process exposure times will depend on load size and are commonly in the range 1 to 3 hours.

FIG. 8 illustrates in diagrammatic form yet another preferred embodiment for practicing the process of the invention. The outer wall of chamber 21 is again formed of metal, such as aluminum or stainless steel maintained at ground potential, and is of similar dimensions to that illustrated in FIG. 4. Mounted within the chamber is a single planar, metallic, electrode 50, preferably constructed of aluminum which may be coated with insulating aluminum oxide to reduce RF sputtering. This electrode is commonly connected to an RF source and carries the work load to be sterilized. This electrode has commonly a total surface area which is at least four times smaller than the total internal surface area of the grounded chamber, to effect a low plasma potential mode of operation. This arrangement, coupled with low power densities (see below) is conducive to very low sterilization temperatures.

This electrical configuration is usually referred to as asymmetric and is conducive to generating an extremely uniform plasma glow filling the entire volume of the processing chamber. It is also responsible for the development of a characteristic accelerating potential at the surface of electrode 50, associated with a thin "dark space" through which positive plasma ions will accelerate and impinge on the electrode and the work load it normally carries.

This arrangement is recommended for hard-to-sterilize materials almost exclusively, particularly for sterilization of metallic devices replete with a high density of cracks and cravices.

The main advantage of this process chamber configuration is its ability to render efficient sterilization at relatively low power densities in the range of 0.0125–0.025 W/cm$^3$. This configuration is also easily scalable as a function of work load size.

This process chamber commonly operates with at least an order of magnitude lower pressure than the pressure for chambers described in FIGS. 1 through 7, while the gas flowrates and gas dispersion tubes 35 are similar to those previously mentioned. To prevent RF sputtering of electrode 50 due to positive ion bombardment, it may either be hard-anodized or alternatively aluminum oxide spray-coated.

One particular sub-configuration to that described in FIG. 8 is illustrated in FIG. 9. In this configuration chamber 21 is water-cooled by cooling coils 28 and contains a perforated metallic enclosure 71 totally surrounding and containing electrode 70. This enclosure may be cooled by coolant-recirculating coils 72 and may be connected to a separate RF source 22a, of a different frequency than that of source 22. This perforated enclosure may be equipped with an open/close hinging mechanism (not shown) to enable access for material to be sterilized to be placed on electrode 70 contained within enclosure 71. This yields the beneficial effect of being able to separately control the abundance of sterilizing active species and their impinging energy.

RF power applied to electrode 70, which may or may not include a negative DC potential from a separate DC supply, (not shown), will control energy of ion impingement, while RF power applied to the auxiliary perforated enclosure 71, will control active species abundance.

It is worth noting that the auxiliary perforated enclosure 71 ought to be of high mesh transparency to allow the plasma glow to extend past it and contact electrode 70. Best operating conditions will be obtained for the smallest surface area of this perforated metallic enclosure. In a few instances, this metallic enclosure was connected to ground, yielding effective sterilization data.

Other configurations are illustrated in FIGS. 10, 11, 12 and 13. These configurations are preferred embodiments for practicing the process of the invention with narrow bore and elongated tubulation, almost exclusively. They are particularly designated for the treatment and sterilization of fiber optics-based tubulations as, for example, endoscopes, proctoscopes, angioscopes or bronohioscopes, having internal diameters as small as 2 mm and an overall length of about 1,000 mm.

The outer wall of elongated chamber 91 is made preferentially of non-metallic material (e.g., glass, ceramic) but, may also be comprised of a metallic/non-metallic structure. The chamber has a minimum internal diameter of one and one half times that of the outside diameter of elongated tubulation 94. The inner and outer surfaces of narrow bore tubulation 94 need to be treated or sterilized. Both ends of narrow and elongated chamber 91 are hermetically plugged with gas permeable but microorganism-impervious membranes 99 (e.g., Tyvek). This arrangement ensures the dynamic flow of an active plasma through and over tubulation 94, and also secures its aseptic condition after sterilization and during prolonged storage.

To effect sterilization or treatment of the inner and outer surfaces of tubulation 94, it is inserted into chamber 91 either bare or sealed within a gas permeable elongated pouch. The chamber is then plugged at both ends with membranes 99.

The chamber is subsequently inserted into exciter coil 92 (FIG. 10) whose terminals are connected to a suitable RF energy source like the one described with respect to FIG. 1.

In another arrangement, the chamber may be inserted within the air gap of capacitive plates 93 (FIG. 11) whose terminals are connected to a suitable RF energy source like the one described with respect to FIG. 1.

Alternatively, chamber 91 may be brought into close proximity to microwave cavity 16 (FIG. 12) whose terminal is connected to a suitable microwave energy source as described with reference to FIG. 3.

Figure 10:
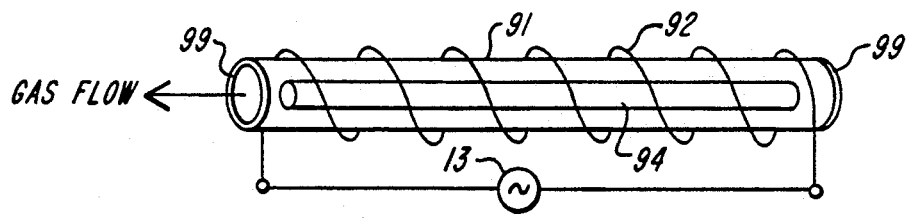
Figure 11:
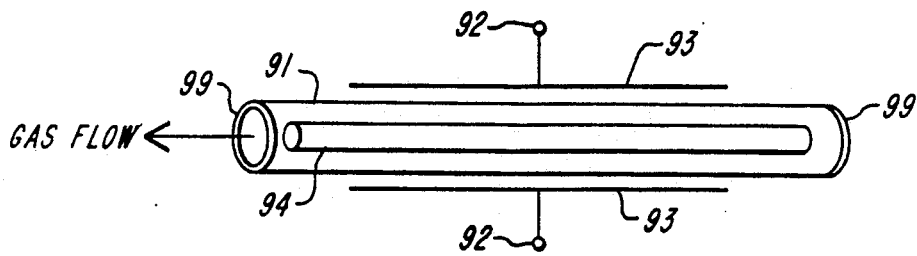
Figure 12:

In cases where the chamber is a metallic—non-metallic structure, the various energy sources described in FIGS. 10, 11 and 12 are coupled to the chamber via the non-metallic portion of the chamber.

In each of the configurations of FIGS. 10, 11 and 12, one end of elongated chamber 91 is temporarily vacuum-flanged to a gas delivery and monitoring system (not shown), while the other free end of the chamber is temporarily vacuum-flanged to a gas exhaust pumping system (not shown).

At the end of the sterilization or treatment cycle, the gas flow and the energy source are turned off, chamber 91 is disengaged from the power source and from both vacuum flanges and stored for future use of narrow bore tubulation 94.

For practical reasons, a plurality of chambers 91 may be employed in a parallel electrical arrangement simultaneously, either in an RF or microwave discharge hook-up.

Figure 13:
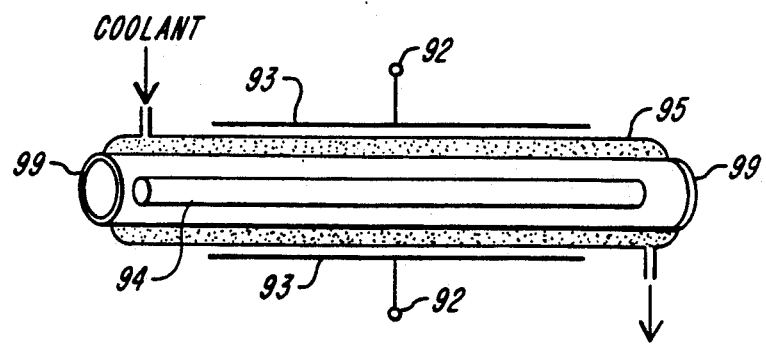

Chamber 91 may have a cooling jacket 95 around it as, for example, shown in FIG. 13. It is not mandatory that exciter coil 92 (FIG. 10) or capacitive plates 93 (FIG. 11) enclose or extend over the entire length of tubulation 94; the latter may be partially contained or not contained at all within coil 92 or capacitor plates 93.

Set forth below are specific examples of suitable operating parameters for effective sterilization employing various apparatus as illustrated in the FIGURES. The particular chamber and corresponding configuration, are referenced in the examples. However, for each of the examples the general technique involved was one in which the material to be sterilized was placed directly in the reaction chamber or placed in a wire basket within the reaction chamber.

The materials used for verification of sterilization effectiveness were "Spordex" bacterial test strips obtained from the American Sterilizer Company, each "Spordex" envelope contained a bacterial strip having an original spore population of $2-4 \times 10^6$ *Bacillus subtilis* var. *niger* per strip or *Bacillus stearothermophilus*. These spore strips were contained in common sterilization efficacy/penetration (towel) test packs according to the standards of the association for the Advancement of Medical Instrumentation (AAMI) guidelines.

For each example the chamber was first evacuated to an initial low pressure level after the materials were placed within it. Hydrogen peroxide vapor was then introduced to the chamber under dynamic flow-through conditions from a liquid source maintained at a constant temperature. The vapor continued to flow through the chamber at a controlled rate to establish both contact with the work load to be sterilized and a steady state reaction pressure. The plasma discharge was then initiated by the application of RF or microwave power as indicated. The discharge was maintained for a controlled time period at the end of which the power was turned off, the vapor flow stopped and the chamber backfilled with air through a bacteria-retentive filter, and later opened and the work load removed. The temperature within the chamber during the process was maintained at less than 70° C., and more typically around 40° C. to 52° C., as sensed by an iron-constantan, type "J", thermocouple circuitry and monitored by an analog or a digital temperature meter.

Alternatively, in-situ reduction of hydrogen peroxide residuals from surfaces previously sterilized followed the sterilization process.

In such cases, at the end of the sterilization process, the power was turned off, hydrogen peroxide flow was stopped, and the chamber evacuated prior to the subsequent introduction of either oxygen or argon gas, or a binary mixture of argon/oxygen at a controlled flow-rate to effect a steady reaction pressure. Radio frequency power was then applied to the chamber creating a gas discharge plasma to effect the reduction of hydrogen peroxide residuals to practically insignificant levels, within less than one hour. The end of this process was marked by RF power and gas flow cut off, followed by immediate chamber backfill with air through a bacteria-retentive filter to atmospheric pressure, enabling the removal of the work load from the chamber.

The spore strips were submitted to an independent testing laboratory which performed a total plate count on the sample strips using a procedure in which 100 milliliters of sterile deionized water were added to each strip in a sterile whirl-pak bag. The bag was then placed in a lab blender for 10 minutes. One 10 milliliter aliquot of sample, a duplicate one milliliter sample, and two consecutive $10^{-1}$ dilutions were plated using Tryptic Soy Agar. The plates were then incubated for 72 hours. After incubation, the plates were read and recorded, and the results calculated on a Colony Forming Unit (CFU) basis.

Alternatively, the spore strips were directly incubated for strict microorganism growth-no growth determinations.

EXAMPLE 1

Effect of hydrogen peroxide ($H_2O_2$) initial concentration (in solution) on sporocidal activity. With metallic chamber and internal perforated shielding electrode, (FIG. 4); metallic chamber dimensions: 18"D×26"L

| Gas: | $H_2O_2$ vapor |
|---|---|
| Dynamic flowrate: | 145 mg/min |
| Pressure: | 0.65 mm Hg |
| RF Power Density: | 0.0224 W/cc |
| Exposure time: | 60 min |
| Maximum processing temperature | 51° C. |

| $H_2O_2$ Initial Concentration in Solution (%) | Percent Kill* (%) |
|---|---|
| 3 | 70 |
| 30 | 97 |
| 50 | 100 |
| 80 | 100 |

For initial bacterial spores populations of 2-4 × $10^6$ spores per strip for both *Bacterium subtilis var. niger* and *stearothermophilus*. These spore strips were contained in common sterilization efficacy/penetration (towel) test packs according to the standards of the Association for the Advancement of Medical Instrumentation, AAMI, guidelines.

EXAMPLE 2

Effect of hydrogen peroxide ($H_2O_2$) dynamic pressure on sporocidal activity. With metallic chamber and fluid-cooled internal perforated shielding electrode, (FIG. 4); metallic chamber dimensions: 18"D×26"L

| Gas: | $H_2O_2$ vapor (initial concentration in solution: 50%) |
|---|---|
| Dynamic flowrate: | 145 mg/min |
| RF Power Density: | 0.0224 W/cc |
| Exposure time: | 60 min |
| Maximum processing temperature: | 49° C. |

| $H_2O_2$ Dynamic Pressure (mm Hg) | Percent Kill* (%) |
|---|---|
| 0.25 | 85 |
| 0.35 | 90 |
| 0.55 | 100 |
| 0.65 | 100 |
| 0.85 | 100 |
| 1.2 | 85 |
| 1.5 | 60 |
| 1.7 | 55 |

*For initial bacterial spores populations of 2-4 × $10^6$ spores per strip for both *Bacterium subtilis var. niger* and *stearothermophilus*. These spore strips were contained in common sterilization efficacy/penetration (towel) test packs according to the standards of the Association for the Advancement of Medical Instrumentation, AAMI, guidelines.

EXAMPLE 3

Effect of hydrogen peroxide ($H_2O_2$) dynamic flowrate on sporocidal activity. With fluid-cooled metallic chamber and fluid-cooled internal perforated shielding electrode, (FIG. 4); metallic chamber dimensions: 18"D×26"L

| Gas: | $H_2O_2$ vapor (initial concentration in solution: 50%) |
|---|---|
| RF Power density: | 0.0207 W/cc |
| Pressure: | 0.65 mm Hg |
| Exposure time: | 60 min |
| Maximum processing temperature: | 48° C. |

| $H_2O_2$ Dynamic Flowrate (mg/min) | Percent Kill* (%) |
|---|---|
| 50 | 60 |
| 80 | 80 |
| 100 | 90 |
| 120 | 100 |
| 140 | 100 |
| 160 | 100 |
| 200 | 100 |

*For initial bacterial spores populations of 2-4 × $10^6$ spores per strip for both *Bacterium subtilis var. niger* and *stearothermophilus*. These spore strips were contained in common sterilization efficacy/penetration (towel) test packs according to the standards of the Association for the Advancement of Medical Instrumentation, AAMI, guidelines.

EXAMPLE 4

Effect of RF power density on sporocidal activity. With metallic chamber and fluid-cooled internal planar electrode surrounded by a perforated shielding enclosure, (FIG. 9). Metallic chamber dimensions: 18"D×26"L. Planar electrode dimensions: 16"W×24"L×¼"thk.

| Gas: | $H_2O_2$ vapor (initial concentration in solution: 50%) |
|---|---|
| Dynamic flowrate: | 145 mg/min |
| Pressure: | 0.65 mm Hg |
| Exposure time: | 60 min |
| Maximum processing temperature: | 48-52° C. |

| RF Power Density (W/cc) | Percent Kill* (%) |
|---|---|
| 0.0172 | 85 |
| 0.0194 | 95 |
| 0.0207 | 100 |
| 0.0224 | 100 |
| 0.0241 | 100 |

*For initial bacterial spores populations of 2-4 × $10^6$ spores per strip for both *Bacterium subtilis var. niger* and *stearothermophilus*. These spore strips were contained in common sterilization efficacy/penetration (towel) test packs according to the standards of the Association for the Advancement of Medical Instrumentation, AAMI, guidelines.

EXAMPLE 5

Effect of hydrogen peroxide ($H_2O_2$) initial concentration (in solution) on sporocidal activity. With elongated, tubular fluid-cooled Pyrex chamber, (FIG. 13). Pyrex chamber dimensions: 2½"D×36"L

| Gas: | $H_2O_2$ vapor |
|---|---|
| Dynamic flowrate: | 145 mg/min |
| Pressure: | 0.65 mm Hg |
| RF power density: | 0.0207 W/cc |
| Exposure time: | 60 min |
| Maximum processing temperature: | 49° C. |

-continued

| H₂O₂ Initial Concentration in Solution (%) | Percent Kill* (%) |
| --- | --- |
| 3 | 65 |
| 30 | 95 |
| 50 | 100 |
| 70 | 100 |
| 80 | 100 |

*Endoscopic PVC lumens (3.5 mm ID × 30" L) directly innoculated with either *Bacterium subtilis var. niger* or *Bacterium sterarothemophilus* at initial spore populations of 4–8 × 10⁶.

EXAMPLE 6

Effect of microwave power density on sporocidal activity. With fluid-cooled metallic chamber and internal perforated metallic shield disc, (FIG. 3). Chamber dimensions: 9"D × 13"L.

| Gas: | H₂O₂ vapor (initial concentration in solution: 50%) |
| --- | --- |
| Dynamic flowrate: | 145 mg/min |
| Pressure: | 0.65 mm Hg |
| Exposure time: | 60 min |
| Maximum processing Temperature: | 42° C. |

| Microwave Power Density (W/cc) | Percent Kill* (%) |
| --- | --- |
| 0.0172 | 80 |
| 0.0195 | 90 |
| 0.0210 | 98 |
| 0.0225 | 100 |
| 0.0240 | 100 |

*For initial bacterial spores populations of 2–4 × 10⁶ spores per strip for both *Bacterium subtilis var. niger* and *stearothermophilus*. These spore strips were contained in common sterilization efficacy/penetration (towel) test packs according to the standard of the Association for the Advancement of Medical Instrumentation, AAMI, guidelines.

What is claimed is:

1. A method for sterilization and treatment of medical and dental devices and materials comprising the steps of, placing said devices and materials within a first metallic perforated electrode, said electrode being positioned within, and spaced from a gas-tight confining chamber, evacuating said chamber to a substantially low pressure and introducing hydrogen peroxide vapor under dynamic flowing conditions to effect contact between said vapor and said medical devices and materials, initiating an electrical discharge in said vapor within said chamber by application of an RF voltage between said internal perforated electrode and the chamber wall, creating a gas plasma accompanied by a substantially field-free and glowless volume within the perforated electrode containing said devices and materials, whereby said devices and materials are contacted by a substantially electrically neutral active species at a temperature below that which would be detrimental to said devices and materials, maintaining said gas plasma for a controlled period of time, maintaining a flow of said vapor through said chamber; and withdrawing said devices and materials from said chamber.

2. A method in accordance with claim 1 wherein said gas tight chamber is formed of metal and is connected to a point of potential reference.

3. A method in accordance with claim 2 wherein said gas-tight confining chamber is fluid cooled.

4. A method in accordance with either of claims 2 or 5 wherein said metallic perforated electrode is fluid cooled.

5. A method for sterilization and treatment of medical and dental devices and materials comprising the steps of, placing said devices and materials within a first metallic perforated electrode, said electrode being positioned within and spaced from a gas-tight confining chamber, said chamber enclosing a second perforated metallic electrode positioned between and spaced apart from said gas-tight chamber and said first perforated electrode, evacuating said chamber to a substantially low pressure and introducing hydrogen peroxide vapor under dynamic flowing conditions to effect contact between said vapor and said medical devices and materials, initiating an electrical discharge in said vapor within said chamber by application of an RF voltage between said second perforated electrode and said chamber wall, creating a gas plasma accompanied by a substantially field-free and glowless volume within said first perforated electrode containing said devices and materials, whereby said devices and materials are contacted by substantially electrically neutral active species at a temperature below that which would be detrimental to said devices and materials, maintaining said gas plasma for a controlled period of time, and maintaining a flow of said vapor through said chamber;

withdrawing said devices and material from said first perforated electrode.

6. A method in accordance with claim 5 wherein said gas-tight confining chamber is made of metal and is connected to a point of potential reference.

7. A method in accordance with claim 6 wherein said gas-tight confining chamber and said first and second metallic perforated electrodes are fluid cooled.

* * * * *